United States Patent [19] [11] 4,283,528
Daniels et al. [45] Aug. 11, 1981

[54] 1-N-AMINOHYDROXYACYL DERIVATIVES OF GENTAMICIN B

[75] Inventors: Peter J. L. Daniels, Cedar Grove; Tattanahalli L. Nagabhushan, Parsippany, both of N.J.

[73] Assignee: Schering Corporation, Kenilworth, N.J.

[21] Appl. No.: 32,808

[22] Filed: Apr. 24, 1979

Related U.S. Application Data

[63] Continuation of Ser. No. 697,298, Jun. 17, 1976, abandoned.

[51] Int. Cl.³ .................. A61K 31/71; C07H 15/22
[52] U.S. Cl. ................................ 536/17 R; 424/180
[58] Field of Search ........................ 536/17 R

[56] References Cited

U.S. PATENT DOCUMENTS

| | | | |
|---|---|---|---|
| 4,002,742 | 1/1977 | Wright et al. | 536/17 |
| 4,029,882 | 6/1977 | Wright | 536/17 |
| 4,104,372 | 8/1978 | Umezawa et al. | 536/10 |

Primary Examiner—Johnnie R. Brown
Attorney, Agent, or Firm—Carver C. Joyner; Bruce M. Eisen; Mary S. King

[57] ABSTRACT

1-N-(R-β-amino-α-hydroxypropionyl) gentamicin B, 1-N-(R-γ-amino-α-hydroxybutyryl) gentamicin B, 1-N-(R-δ-amino-α-hydroxyvaleryl) gentamicin B and the corresponding diastereoisomers derived from the respective S-aminohydroxy acids and the acid addition salts thereof exhibit substantial antibacterial activity, especially against strains of bacteria which are resistant to gentamicin B and acid addition salts thereof.

11 Claims, No Drawings

1-N-AMINOHYDROXYACYL DERIVATIVES OF GENTAMICIN B

This is a continuation, of application Ser. No. 697,298 filed June 17, 1976, now abandoned.

This invention relates to 1-N-aminohydroxyacyl derivatives of gentamicin B. More specifically, this invention relates to 1-N-(R-β-amino-α-hydroxypropionyl) gentamicin B, 1-N-(R-γ-amino-α-hydroxybutyryl) gentamicin B, 1-N-(R-δ-amino-α-hydroxybutyryl) gentamicin B, 1-N-(R,S-β-amino-α-hydroxypropionyl) gentamicin B, 1-N-(R,S-γ-amino-α-hydroxybutyryl) gentamicin B, and 1-N-(R,S-δ-amino-α-hydroxyvaleryl) gentamicin B. This invention also relates to acid addition salts of the compounds and to methods for using said compounds as antibacterial agents.

PRIOR ART

Gentamicin B, its isolation and purification are described in U.S. Pat. No. 3,915,955, which issued Oct. 28, 1975. The compound is coproduced with gentamicin C complex during the fermentation of certain species of the genus Micromonospora, e.g. M. purpurea NRRL 2953.

In the Journal of Antibiotics (Japan) 25:695-708 (1972) Hiroshi Kawaguchi and his coworkers at Bristol-Banyu Research Institute described the preparation and antibacterial profile of 1-N-(S-γ-amino-α-hydroxybutyryl) kanamycin A which they designated BB-K8 (now also known as amikacin). In a subsequent publication, the researchers prepared and tested the R-diastereoisomer of BB-K8, as well as the R,S mixture thereof, and found that these configurational isomers exhibited one-fourth (¼) and one-half (½) the activity of BB-K8, respectively. This work was published in Journal of Antibiotics 26:297-301 (1973). About the same time, T. H. Haskell, et al. published the results they obtained by replacing the 1-N-(S-γ-amino-α-hydroxybutyryl) side chain of butirosin with other acyl groups including the 1-N-R-configurational isomer and concluded inter alia that, "the enantiomorphic (R)-derivative (24) was significantly less active than its optical antipode . . . the (S)-configuration was required for maximum activity" . . . These results were published in Carbohydrate Research, 28 (1973) 263-280. Hamao Umezawa et al. have disclosed that 1-N-isoserylkanamycin A, 1-N-isoserylkanamycin B and 1-N-isoseryl-3',4'-dideoxykanamycin B are active against kanamycin resistant strains of *Escherichia coli* and *Pseudomonas aeruginosa*. It was also disclosed that such activity is exhibited by derivatives of the (R) or (S) forms of the aminohydroxy acids as well as by the derivative of the R,S acid. These findings are set forth in U.S. Pat. No. 3,939,143, issued Feb. 17, 1976.

In view of the foregoing, it is obvious that the D and DL forms of 1-N-aminohydroxyacyl derivatives of aminoglycoside antibiotics are not necessarily more active than the underivatized (parent) antibiotic. Further, it is also obvious that structure-activity relationship of such derivatives are not consistant and, therefore, one skilled in the art cannot predict what, if any, antibacterial effect the derivatives will exhibit, or if the products derived from the R-form, S-form or the R,S-mixture of the aminohydroxy acids will exhibit the same antibacterial activity or if one form will exhibit a significantly improved antibacterial activity over the other form. We have discovered that the R, and R,S-aminohydroxyacyl derivatives of gentamicin B have essentially the same favorable biological properties as the S-isomer; a finding which was not predictable and is unobvious in view of the prior art publications.

Thus, the invention sought to be patented resides in compounds selected from the group consisting of 1-N-(R-β-amino-α-hydroxypropionyl) gentamicin B, 1-N-(R,S-β-amino-α-hydroxypropionyl) gentamicin B, 1-N-(R-γ-amino-α-hydroxybutyryl) gentamicin B, 1-N-(R,S-γ-amino-α-hydroxybutyryl) gentamicin B, 1-N-(R-δ-amino-α-hydroxyvaleryl) gentamicin B, 1-N-(R,S-δ-amino-α-hydroxyvaleryl) gentamicin B, and the non-toxic pharmaceutically acceptable acid addition salts thereof.

The compounds of this invention may be prepared by processes which are analogous to those set forth in the aforementioned prior art publications. However, applicants prefer to utilize the following modes of preparation:

PREPARATION I

3,6'-Di-N-Benzyloxycarbonylgentamicin B from gentamicin B

Add cupric acetate hydrate (8 gms., 40 mmol) and nickel (II) acetate tetrahydrate (9.92 gms., 40 mmol) to a stirred solution of gentamicin B (9.64 gms., 20 mmol) in dimethylsulfoxide (400 ml.). Stir at room temperature for 30 minutes, then to the cupric-nickel (II) salt complex thereby formed add N-benzyloxycarbonyloxyphthalimide (14 gms., 47.2 mmol) in dimethylsulfoxide (70 ml.) dropwise over a 10 minute period. Stir for one hour at room temperature, then pour the reaction mixture into ether (4.1) and shake for one minute. Allow the oil to settle and decant off the supernatant ether. Repeat this procedure two more times using 1500 ml. and 1000 ml., respectively, of diethyl ether. Dissolve the resultant gummy residue thereby obtained in methanol (400 ml.) and concentrated ammonium hydroxide (40 ml.) and bubble hydrogen sulfide through the solution, separate the resultant precipitate comprising cupric sulfide and nickel sulfide by filtration through a pad of Celite. Wash the residue with methanol, then stir the combined filtrate and methanol wash with Amberlite IRA-401S (OH⊖)ion exchange resin (400 ml.) to remove the N-hydroxy phthalimide. Filter the solution, wash the resin with methanol, then evaporate the combined filtrate and methanol wash in vacuo, and chromatograph the resultant residue on silica gel (900 gms.) eluting with chloroform:methanol:concentrated ammonium hydroxide (30:10:1). Combine the like fractions containing the desired product as determined by thin layer chromatography and evaporate the combined fractions in vacuo to a residue comprising the 3,6'-di-N-benzyloxycarbonylgentamicin B; yield 10.86 gms. (75% theory); $[\alpha]_D^{26} + 105.3°$ (c, 4.07 in water).

Analysis calculated for $C_{35}H_{50}O_{14}N_4 \cdot CO_2 \cdot 2H_2O$: C, 52.04; H, 6.55; N, 6.74%.

Found: C, 51.94; H, 6.33, N, 6.83%.

In a similar manner is prepared 3,6'-di-N-tert.-butoxycarbonylgentamicin B: $[\alpha]_D^{26} + 113.3°$ (c, 0.39 in water); pmr (ppm) (D₂O): δ1.17 (4"-C-$\underline{CH_3}$); 1.38 (t-butyl); 2.5 (3"-N-$\underline{CH_3}$); 2.54 (H-3", $J_{2'',3''} = 10$ Hz); 4.02 (H-5" eq, $J_{5''}$ ax,eq = 12 Hz); 5.04 (H-1", $J_{1'',2''} = 3.5$ Hz); 5.23 (H-1', $J_{1,2'} = 3.0$ Hz).

PREPARATION II

6'-N-Tert.-Butoxycarbonylgentamicin B

Add cupric acetate hydrate (24 gms. 120 mmol) to a stirred solution of gentamicin B (19.28 gms., 40 mmol) in dimethylsulfoxide (1 liter). Continue stirring for 20 minutes, to the cupric salt complex thereby formed in situ add a solution of N-tert.-butoxycarbonyloxyphthalimide (16 gms., 61 mmol) in dimethylsulfoxide (200 ml.) over a period of 20 minutes. Stir for 18 hours at room temperature, then bubble hydrogen sulfide through the solution to precipitate cupric sulfide. Remove the solids by filtration through a pad of Celite and wash the residue with 200 ml. of water. Stir the combined filtrate and washings with 200 ml. of Amberlite IRA-401S (OH⊖) ion exchange resin for one hour. Remove the resin by filtration, wash with water, and concentrate the combined filtrate and washings in vacuo using benzene to azeotrope with water. Dissolve the resultant residue in methanol and pour the methanol solution into excess ether with stirring. Filter and air dry the resultant precipitate comprising 6'-N-tert.-butoxycarbonylgentamicin B, yield 23 gm. (100% theory); $[\alpha]_D^{26} +124°$ (c, 1 in methanol). pmr (ppm) (D$_2$O): δ1.21 (4''-C-CH$_3$); 1.42 (t-butyl); 2.55 (3''-N-CH$_3$); 5.06 (H-1'', $J_{1'',2''}=4.0$ Hz); 5.21 (H-1', $J_{1',2'}=(3.0$ Hz). Analysis calculated for $C_{24}H_{46}N_4O_{12}\cdot CO_2\cdot H_2O$: C, 46.57; H, 7.51; N, 8.68%. Found: C, 46.80; H, 7.82; N, 8.54%.

The foregoing blocked gentamicin B derivatives may be reacted with a suitably protected R,S-β-amino-α-hydroxypropionic acid (HAPA), a suitably protected R,S-γ-amino-α-hydroxybutyric acid (HABA) or a suitably protected R,S-δ-amino-α-hydroxyvaleric acid (HAVA), preferably in the form of an activated ester, to form a blocked 1-N-R,S-HAPA gentamicin B, a blocked 1-N-R,S-HABA gentamicin B, or a blocked 1-N-R,S-HAVA gentamicin B. Similarly, the corresponding 1-N-R-HAPA gentamicin B, 1-N-R-HABA gentamicin B, or 1-N-R-HAVA gentamicin B may be prepared by reacting gentamicin B blocked as described above with a suitably protected activated derivative of R-β-amino-α-hydroxypropionic acid, R-γ-amino-α-hydroxybutyric acid, or δ-amino-α-hydroxyvaleric acid which may be obtained by resolution of a racemic mixture of the respective N-protected acids by means generally known in the art, followed by the preparation of a suitably protected activated derivative thereof.

Alternatively, 1-N-R-HAPA gentamicin B, 1-N-R-HABA gentamicin B or 1-N-R-HAVA gentamicin B may be prepared by reacting a suitably N-protected activated ester derivative of a racemic mixture of the respective acids with the above 3,6' or 6' blocked gentamicin, B followed by chromatographically separating the blocked 1-N-R-HAPA gentamicin B, the 1-N-R-HABA gentamicin B or the 1-N-R-HAVA gentamicin B from the corresponding diastereoisomer. The 1-N-R-HAPA gentamicin B, the 1-N-R-HABA gentamicin B, or the 1-N-R-HAVA gentamicin B so obtained is deblocked by a method generally known in the art to yield the desired 1-N-R acyl derivative of gentamicin B.

The preparation of suitably protected activated derivatives of the above-named acids are known in the art. However, in preparation III is set forth a procedure for preparing such a derivative of R-δ-amino-α-hydroxypentanoic acid:

PREPARATION III

N-[R-5-benzyloxycarbonylamino-2-hydroxypentanoyloxy]succinimide

R-5-amino-2-hydroxypentanoic acid is prepared by diazotization of D-ornithine as described by J. P. Greenstein et al "Chemistry of Amino Acids", Vol. 3 2477–2491 (1961).

The benzyloxycarbonyl derivative of the acid is prepared in a manner analogous to that described for preparing same derivative of S-5-amino-2-hydroxypentanoic acid by Haskell et al in *Carbohydrate Research*, 28 263 (1973).

Treat R-5-benzyloxycarbonyl-amino-2-hydroxypentanoic acid (5.34 g, 20 mmol.) in dry tetrahydrofuran (160 ml.) with N-hydroxysuccinimide (2.31 g, 20 mmol.) and dicyclohexylcarbodiimide (4.12 g., 20 mmole.). Allow the mixture to stand at 0°–5° for 16 hours then remove the dicyclohexylurea by filtration. Concentrate the filtrate to dryness and dry the product in high vacuum to obtain thereby N-[R-5-benzyloxycarbonylamino-2-hydroxypentanoyloxy]succinimide.

In a similar manner is prepared N-[R,S-5-benzyloxycarbonylamino-2-hydroxypentanoyloxy]succinimide when D,L-ornithine is substituted for D-ornithine and the above procedure is utilized.

As previously stated, this invention also embraces the non-toxic pharmaceutically acceptable acid addition salts of 1-N-R-HAPA gentamicin B, 1-N-R,S-HAPA gentamicin B, 1-N-R-HABA gentamicin B and 1-N-R,S-HAVA gentamicin B. The preferred non-toxic pharmaceutically acceptable acid addition salts are those derived from inorganic acids, such as hydrochloric, phosphoric and, especially, sulfuric acid. The salts may be prepared by titrating an aqueous solution of antibacterial agent with about 1 N acid to pH 4.0 followed by lyophilization of the resulting solution. The salts may also be obtained by precipitation from the aqueous solution by the addition of a water miscible precipitant such as alcohol (e.g. methanol) or a ketone (e.g. acetone).

The following examples are set forth to exemplify this invention, and should not be construed as limiting same.

EXAMPLE 1

1-N-(R-β-Amino-α-Hydroxypropionyl)-gentamicin B

To a solution of 3,6'-di-N-benzyloxycarbonyl gentamicin B (3.75 g., 5 mmol.) in methanol (25 ml.) and water (25 ml.), add with stirring a solution of N-(R-β-benzyloxycarbonylamino-α-hydroxypropionyloxy) succinimide (2.18 g., 6.5 mmol.) in dimethylformamide (12 ml.). Stir the reaction mixture for 2 hours, concentrate in vacuo, and dissolve the resultant residue in water (75 ml.) and methanol (75 ml.). Hydrogenate in the presence of 5% palladium-on-carbon (5 g.) at 50 psi for 24 hours. Remove the catalyst by filtration through a pad of Celite (Celite is the tradename of diatomaceous earth product of Johns-Manville, Manville, N.J.) and wash with water. Concentrate the combined filtrate and washings and chromatograph the resultant residue on Dowex 1-X2 ion exchange resin in the hydroxide form (200 g., 200–400 mesh), (Dowex is the tradename of ion exchange resins produced by Dow Chemical Co., Midland, Mich.) eluting with water. Combine the like fractions containing 1-N-(R-β-amino-α-hydroxypropionyl)-gentamicin B as determined by thin layer chromatography on silica gel using chloroform:methanol:ammonium hydroxide (3:4:2) as the solvent system. Concentrate to a small volume, dilute with water and lyophilize to obtain 1-N-(R-β-amino-α-hydroxypropionyl) gentamicin B, yield 1.7 g. (60% theory).

EXAMPLE 2

1N-(R-γ-Amino-α-hydroxybutyryl) gentamicin B

To a solution of 3,6'-di-N-tert.-butoxycarbonyl gentamicin B (3.41 g., 5 mmol.) in methanol (25 ml.) and water (25 ml.), add with stirring a solution of N-(R-γ-benzyloxycarbonylamino-α-hydroxybutyryloxy) succinimide (1.8 g., 5 mmol). in dimethylformamide (10 ml.). Stir the reaction mixture for 6 hours, concentrate in vacuo, and chromatograph the residue on silica gel (60–200 mesh, 300 g.) using a solvent system comprising chloroform, methanol and ammonium hydroxide 30:10:0.25, combine the fractions 78–140 (10 ml.-fractions) and concentrate in vacuo. Rechromatograph the residue on the same column using the same solvent system and obtain pure 1-N-(R-γ-N-benzyloxycarbonylamino-α-hydroxybutyryl)-3,6'-di-N-tert.-butoxycarbonyl gentamicin B, by evaporating fractions 75–147 to dryness in vacuo. Dissolve the residue in 50% aqueous methanol (20 ml.) and hydrogenate over 5% palladium-on-carbon catalyst (0.2 g.) at room temperature and 50 psi for 24 hours. Remove the catalyst by filtration through a pad of Celite, wash with water and evaporate the combined filtrate to dryness. Dissolve the product in trifluoroacetic acid (2.5 ml.) and set aside for 3 minutes. Add excess ether to precipitate the trifluoroacetic acid salt of the product and isolate by filtration, wash with ether and dry. Dissolve the solid in water (10 ml.) and stir with just enough Amberlite IRA-401S (OH$^-$) ion exchange resin (Amberlite is the tradename of ion exchange resins produced by Rohm and Haas Co., Philadelphia, Pa.) to bring the pH to 9.5, remove the resin by filtration, wash with water and lyophilize to combined filtrates to give pure 1-N-(R-γ-amino-α-hydroxybutyryl) gentamicin B, yield 0.6 g.; $[\alpha]_D^{26}+118.1°$ (c, 1 in water) pmr (ppm) (D$_2$O): δ1.23 (4''-C-CH$_3$); 2.66 (3''-N-CH$_3$); 4.2 (H-2'', J=5 Hz 3 Hz) 5.03 H-1'', J=4 Hz); 5.4 (H-1', J=3.5 Hz).

Analysis calculated for C$_{23}$H$_{45}$O$_{12}$N$_5$3CO$_2$4H$_2$O; C, 39.64; H, 6.78; N, 8.89%.

Found: C, 39.88; H, 6.58; N, 9.28%.

EXAMPLE 3

A. 1-N-(R,S-β-Amino-α-Hydroxypropionyl) gentamicin B

To a stirred solution of 3,6'-di-N-benzyloxycarbonyl-gentamicin B (1 g., 1.33 mmol.) in methanol (5 ml.) and water (5 ml.) add a solution of racemic N-(benzyloxycarbonylamino-α-hydroxypropionyloxy) succinimide (0.674 g., 0.2 mmol). in dimethylformamide (2 ml.). Stir for 2 hours, then evaporate the solvent in vacuo.

B. Dissolve the residue in methanol (10 ml. and water (10 ml.) and hydrogenate in the presence of 5% palladium-on-charcoal catalyst at 55 psi for 24 hours. Remove the catalyst by filtration through Celite, wash with water and evaporate the filtrate and washes to a residue.

C. Chromatograph the residue on silica gel (60–100 mesh, 50 g.) eluting with a mixture of chloroform:methanol:ammonium hydroxide (3:4:2). Monitor the fractions by thin layer chromatography on silica gel using chloroform:methanol:ammonium hydroxide (3:4:2) as the solvent system. Combine like fractions and evaporate in vacuo to a residue. Dissolve the residue in water and lyophilize to obtain thereby 1-N-(R,S-β-amino-α-hydroxypropionyl) gentamicin B.

1-N-(R,S-γ-Amino-α-Hydroxybutyryl) gentamicin B

In a manner similar to that described in Example 3, treat 3,6'-di-N-benzyloxycarbonylgentamicin B with racemic N-(α-benzyloxycarbonylamino-α-hydroxybutyryloxy) succinimide, isolate and hydrogenate the resultant intermediate in a manner similar to that described in said Example 3 to obtain 1-N-(R,S-γ-amino-α-hydroxybutyryl) gentamicin B.

EXAMPLE 4

1-N-(R-δ-amino-α-hydroxypentanoyl) gentamicin B

To a solution of 3,6'-di-N-benzyloxycarbonylgentamicin B (0.75 g. 1 mmol.) (prepared by the Procedure of Preparation 1) in methanol:water (3:1, 35 ml.) containing triethylamine (0.152 g.) add a solution of N-[R-δ-benzyloxycarbonylamino-α-hydroxypentanoyloxy] succinimide (0.528 g. 1.5 mmol.) in dimethylformamide (7 ml.). Stir the mixture at 5° for 2 hours, then evaporate to dryness. Chromatograph the residue on 50 g. of silica gel, eluting with a 27:11:2.6 chloroform:methanol:ammonium hydroxide solvent system. Monitor the fractions by TLC and combine and evaporate appropriate fractions containing the major reaction product. Dissolve this product in 1:1 aqueous dioxane (20 ml.) and hydrogenate over a 10% palladium on carbon catalyst (75 mg.) at 55 p.s.i. Filter off the catalyst and evaporate the filtrate to dryness. Dissolve the residue thereby obtained in water and pass through an IR 401 S resin column (hydroxide ion cycle). Collect the eluate and lyophilize to obtain the title compound as a white amorphous solid.

Yield: Ca0.2 g.

In a similar manner, by using N-[R,S-δ-benzyloxycarbonylamino-α-hydroxypentanoyloxy] succinimide in the foregoing example and by following the procedure thereof, 1-N-(R,S-δ-amino-α-hydroxypentanoyl) gentamicin B may be prepared.

EXAMPLE 5

Non-Toxic Pharmaceutically Acceptable Acid Addition Salts

A. Sulfate Salts (Sulfuric Acid Addition Salts)

Dissolve 5.0 g. of either 1-N-(R-β-amino-α-hydroxypropionyl) gentamicin B or 1-N-(R,S-β-amino-α-hydroxypropionyl) gentamicin B in 25 ml. of water and adjust the pH of the solution to 4.0 with 1 N sulfuric acid with stirring. Dilute to 100 ml. and lyophilize. In like manner, the sulfate salt of 1-N-(R-γ-amino-α-hydroxybutyryl) gentamicin B or 1-N-(R,S-γ-amino-α-hydroxybutyryl) gentamicin B may be prepared.

B. Hydrochloride Salts

Dissolve 5.0 g. of either 1-N-(R-β-amino-α-hydroxypropionyl) gentamicin B or 1-N-(R,S-β-amino-α-hydroxypropionyl) gentamicin B in 25 ml. of water. Acidify with 2 N hydrochloric acid to pH 4.0. Lyophilize the acidified solution to obtain the corresponding 1-N-(R-β-amino-α-hydroxypropionyl) gentamicin B or 1-N-(R,S-β-amino-α-hydroxypropionyl) gentamicin B or hydrochloric acid addition salt.

In like manner, the hydrochloric acid addition salt of 1-N-(R-γ-amino-α-hydroxybutyryl) gentamicin B or 1-N-(R,S-γ-amino-α-hydroxybutyryl) gentamicin B may be prepared.

The compounds of this invention are broad spectrum antibacterial agents possessing improved antibacterial activities compared to the parent antibiotic, i.e. gentamicin B. This improved activity is specifically manifest in the improved activity of the claimed compounds against organisms resistant to the parent compound. Thus, for example, the compounds of this invention are more active against organisms which inactivate the parent antibiotic by acetylation of the 3-amino group and/or by adenylylation of the 2''-hydroxyl group. Thus, the compounds of this invention are potentially commercially important antibacterial agents and may be employed for the antibacterial uses and under substantially the same conditions described for gentamicin B in U.S. Pat. No. 3,915,955 (issued Oct. 28, 1975). The compounds of this invention may be employed in the form of topical preparations, or preferably, as parenteral preparations wherein hydrolysis of the 1-N-acyl function does not occur, e.g. in substantially neutral parenteral preparations.

We claim:

1. A compound selected from the group consisting of 1-N-(R-β-amino-α-hydroxypropionyl-gentamicin B, 1-N-(R-γ-amino-α-hydroxybutyryl) gentamicin B, 1-N-(R-δ-amino-α-hydroxyvaleryl) gentamicin B, the respective R,S diastereoisomeric mixtures of said compounds and the non-toxic pharmaceutically acceptable acid addition salts thereof.

2. A compound of claim 1, said compound being 1-N-(R-β-amino-α-hydroxypropionyl) gentamicin B.

3. A compound of claim 1, said compound being 1-N-(R-γ-amino-α-hydroxybutyryl) gentamicin B.

4. A compound of claim 1, said compound being 1-N-(R-δ-amino-α-hydroxyvaleryl) gentamicin B.

5. The R,S-diastereoisomeric mixture 1-N-(R,S-β-amino-α-hydroxypropionyl) gentamicin B.

6. The R,S-diastereoisomeric mixture 1-N-(R,S-γ-amino-α-hydroxybutyryl) gentamicin B.

7. The R,S-diastereoisomeric mixture 1-N-(R,S-δ-amino-α-hydroxyvaleryl) gentamicin B.

8. A non-toxic pharmaceutically acceptable acid addition salt of a compound of claim 1.

9. A compound of claim 8, said compound being 1-N-(R,β-amino-α-hydroxypropionyl) gentamicin B sulfate.

10. A compound of claim 8, said compound being 1-N-(R-γ-amino-α-hydroxybutyryl) gentamicin B sulfate.

11. A compound of claim 8, said compound being 1-N-(R-δ-amino-α-hydroxyvaleryl) gentamicin B sulfate.

* * * * *